United States Patent [19]

Iemura et al.

[11] Patent Number: 4,877,790
[45] Date of Patent: Oct. 31, 1989

[54] QUINAZOLINE DERIVATIVE, PROCESSES FOR ITS PRODUCTION, AND CEREBRAL DYSFUNCTION REMEDYING AGENT COMPRISING IT AS ACTIVE INGREDIENT

[75] Inventors: Ryuichi Iemura, Toyonaka; Manabu Hori, Osaka; Hiroshi Ohtaka, Osaka; Takayuki Sukamoto, Osaka; Hideaki Hara, Osaka; Keizo Ito, Osaka, all of Japan

[73] Assignee: Kanebo Limited, Toky, Japan

[21] Appl. No.: 134,302

[22] Filed: Dec. 15, 1987

[30] Foreign Application Priority Data

Aug. 10, 1987 [JP] Japan .................. 62-200510

[51] Int. Cl.$^4$ .................. A61K 31/505; C07D 239/84
[52] U.S. Cl. .................. 514/260; 514/259; 544/283; 544/287; 544/293
[58] Field of Search .................. 544/287; 514/260

[56] References Cited

U.S. PATENT DOCUMENTS 3,609,152 9/1971 Hess et al. .................. 260/256.5 R
3,812,127 5/1974 Cronin et al. .................. 544/287
4,588,725 5/1986 Neumann .................. 544/287
4,672,116 6/1987 Bandurco et al. .................. 544/287

Primary Examiner—Glennon H. Hollrah
Attorney, Agent, or Firm—Wenderoth, Lind & Ponack

[57] ABSTRACT

A quinazoline derivative represented by the following formula (I)

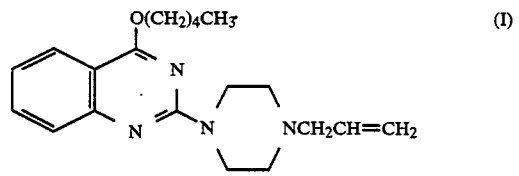

or its pharmacologically acceptable acid addition salt and processes for production thereof. The quinazoline compound is used as a cerebral dysfunction remedying agent.

2 Claims, No Drawings

QUINAZOLINE DERIVATIVE, PROCESSES FOR ITS PRODUCTION, AND CEREBRAL DYSFUNCTION REMEDYING AGENT COMPRISING IT AS ACTIVE INGREDIENT

This invention relates to a novel quinazoline derivative, processes for its production and a drug comprising it as an active component. More specifically, it relates to a quinazoline derivative represented by the following formula (I)

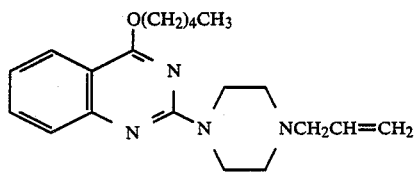

or its pharmacologically acceptable acid addition salt, processes for its production, and a cerebral dysfunction remedying agent comprising it as an active ingredient.

An increase in the number of patients with cerebral dysfunction, such as senile dementia, has become a major social issue as a result of a rapid increase in the population of aged people. Dementia can be pathologically classified into two main types, dementia associated with cerebrovascular diseases and senile dementia of the Alzheimer type. Both types of dementia are characterized mainly by marked impairment of intellectual function such as memory and orientation which are associated with organic degeneration of the brain. In addition, abnormal behaviors such as nocturnal delirium, hyperkinesis, fugue and aggression are observed. The cerebrovascular dementia is caused by cerebrovascular diseases such as cerebral infarction and cerebral hemorrahage. It is well known that the brain is a metabolically active organ and that its function is rapidly lost when the brain is exposed to a hypoxic condition induced by a disorder in cerebral circulation. In fact, as one animal model, the exposure of the animal to the hypoxic condition is used to induce deficits in learning and memory. The brain protective action of a drug against the hypoxic condition has been investigated in order to prevent brain dysfunction. From a biochemical point of view, the influence of lipid peroxides formed during cerebral ischemia has been cited as one cause of cerebral dysfunction. Thus, a drug which can inhibit lipid peroxide formation is thought to be effective for treatment of cerebral dysfunction. A decrease in activity in the acetylcholine nervous system was advocated as a cause of dementia of the Alzheimer type, and amnesia induced by scopolamine, which is an acetylcholine receptor antagonist, was cited as one animal model of the Alzheimer-type dementia.

Accordingly, it may be said that a drug which has a remedying action on hypoxia-induced deficits in learning and memory, a brain protective action in the hypoxic condition, and an anti-scopolamine induced amnesia effect will be useful as a remedying agent for cerebral dysfunction.

It is an object of this invention to provide a cerebral dysfunction remedying agent.

Another object of this invention is to provide a drug which is useful for remedying cerebral dysfunction in senile dementia.

Still another object of this invention is to provide a novel compound having various activity spectra for remedying cerebral dysfunction.

Yet another object of this invention is to provide a process for producing the above compound of the invention.

A further object of this invention is to provide an intermediate for the production of the compound of the invention.

Other objects of the invention along with its advantages will become apparent from the following description.

According to this invention, the above objects and advantages of this invention are firstly achieved by a quinazoline derivative represented by the following formula (I)

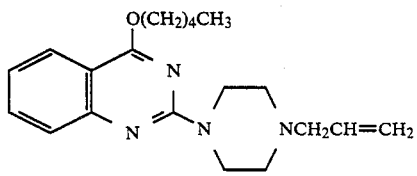

or its pharmacologically acceptable acid addition salt.

The pharmacologically acceptable acid addition salt of the compound of this invention includes, for example, its hydrochloride, sulfate, maleate and furmarate.

The compound of formula (I) provided by this invention can be produced by processes A, B and C below.

Process A will first be described.

Process A

Process A comprises reacting a compound of the following formula (II)

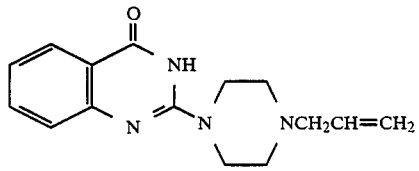

with a compound represented by the following formula (III)

wherein X represents a halogen atom.

Specifically, the compound of formula (I) provided by this invention can be obtained by reacting the compound (II) with an equivalent mole or a slightly excessive amount, usually 1 to 1.5 equivalents, of the compound (III) in an inert organic solvent in the presence of a base at 0° to 100° C. for 1 to 5 hours. N,N-dimethylformamide and N-methylpyrrolidone, for example, may be used as the inert organic solvent. Examples of the base used are sodium hydride and potassium hydride.

The compound (II) used as a starting material in process A is a novel substance, and can be produced, for example, by reacting a compound of the following formula (IV)

(IV)

[structure: benzaldehyde with ortho N=C-Y, C=O NH]

wherein Y represented a chlorine atom or a lower alkylthio group,
with a compound of the following formula (V)

$$HN\diagdown NCH_2CH=CH_2 \quad (V)$$

Specifically, the compound (II) can be produced by reacting the compound (IV) with usually 1 to 8 equivalents of the compound (V) in the absence of solvent, or in an inert organic solvent such as toluene, xylene and ethanol at room temperature to 200° C. for 3 to 10 hours.

Process B will now be described.

Process B

Process B comprises reacting a compound of the following formula (VI)

(VI)

[structure: 4-chloroquinazoline with 2-piperazinyl-allyl]

with a compound of the formula $$CH_3(CH_2)_4OH \quad (VII).$$

Specifically, the compound (I) can be obtained by reacting the compound (VI) with an equivalent mole or a slightly excessive amount, usually 1 to 1.5 equivalents, of the compound (VII) in an inert organic solvent in the presence of a base at 0° to 100° C. for 1 to 5 hours. Examples of the inert organic solvent are N,N-dimethylformamide and N-methylpyrrolidone. The base used may, for example, be metallic sodium, sodium hydride or potassium hydride.

The compound (VI) used as a starting material in process B is a novel substance, and can be produced, for example, by heating a compound of the following formula (II)

(II)

[structure as in II]

in phosphorus oxychloride.

Process C will be described.

Process C

Process C comprises reacting a compound of the following formula (VIII)

(VIII)

[structure: quinazoline with O(CH2)4CH3 and Cl]

with a compound of the following formula (V)

$$HN\diagdown NCH_2CH=CH_2 \quad (V)$$

Specifically, the compound (I) of the invention can be obtained by reacting the compound (VIII) with 1 to 4 equivalents of the compound (V) in the absence of solvent or in an inert organic solvent such as toluene, xylene, ethanol or dichloroethane at room temperature to 200° C. for 1 to 5 hours.

The compound (VIII) used as a starting material in process C is a novel substance, and can be produced, for example, by reacting a compound represented by the following formula (IX)

(IX)

[structure: 4-chloro-2-chloroquinazoline]

with a compound of the formula $$CH_3(CH_2)_4OH \quad (VII).$$

Specifically, the compound (VIII) can be produced by reacting the compound (IX) with an equivalent mole or a slightly excessive amount, usually 1 to 1.5 equivalents, of the compound (VII) in an inert organic solvent in the presence of a base at 0° to 100° C. for 0.5 to 3 hours. Examples of the inert organic solvent are N,N-dimethylformamide and N-methylpyrrolidone, and examples of the base are sodium hydride and potassium hydride.

The compound of formula (I) produced by the above processes may, as required, be converted into a pharmacologically acceptable acid addition salt by reaction with an acid in a customary manner.

For use in remedying cerebral dysfunction in senile dementia, the compound of this invention may be formulated into usual dosage forms and used orally or parenterally.

For oral administration, the dosage forms may, for example, be solid preparations such as tablets, granules, powders or capsules, and liquid preparations such as a syrup. These preparations may be produced by conventional methods. The solid preparations may be produced by using ordinary pharamceutical adjuvants such as lactose, corn starch, crystalline cellulose and talc. The capsules may be obtained by filling granules, powders, etc. so produced into suitable capsules. The syrup may be obtained by dissolving or suspending the compound of this invention in an aqueous solution of sugar or carboxymethyl cellulose, for example.

An injectable preparation, for example, may be used for parenteral administration. It may be prepared by a conventional method using, as required, a stabilizer, a dissolving aid, etc.

The dosage of the compound of this invention may vary depending upon the condition, body weight, age, etc. of the patient. Usually, it is 3 to 300 mg per day for adults and the compound in this dosage is adminstered once, or dividedly two to three times, per day.

The compound of this invention (dihydrochloride) was tested for the activity of remedying hypoxia-induced disturbances in learning and memory (anti-$CO_2$-induced amnesia activity), the activity of protecting brain in hypoxia (anti-hypoxic activity), the activity of inhibiting formation of lipd peroxides (antioxidant activity), the anti-scopolamine-induced amnesia activity, and acute toxicity, and the results are shown below.

TEST EXAMPLE 1

Anti-$CO_2$-induced amnesia activity (the activity of remedying hypoxia-induced deficits in learning and memory):

Testing method

Male mice of the ddY strain (body weight 20-30 g, 30 per group) were used. Anti-$CO_2$-induced amnesia activity was determined by using one-trial passive avoidance response as an index.

The experimental device consisted of two compartments, one illuminated and the other dark, with a guillotine door in the boundary of the two compartments permitting free passage of the mice through it.

In an acquisition trial, a mouse was placed in the illuminated compartment and allowed to enter the dark one. As soon as the mouse entered the dark compartment, the door was shut, and an electrical shock (0.5 mA, 0.2 sec.) was applied through the grid floor. Thus, the mouse was caused to learn that it receives an electric shock upon entering the dark room. In a retrieval trial, the mouse was again placed in the illuminated compartment 24 hours after the acquisition trial, and the time elapsed until it entered the dark compartment (response latency) was measured to an extent of 300 seconds at the longest. (One-trial passive avoidance response).

Treatment of inducing amnesia by carbon dioxide was performed by putting the mouse in a 1.6-liter plastic container having a gas intake opening and an gas discharging opening immediately after the acquisition trial, and passing 100% carbon dioxide gas for 14 seconds at a flow rate of 8 liters/min.

The compound of this invention (dihydrochloride) was dissolved in a 1% gum arabic solution, and orally administered to the animals 60 minutes before the acquisition trial. A 1% gum arabic solution alone was administered to the control group.

Test results

The results are shown in Table 1.

TABLE 1

| Test compound | Dose (mg/kg) | Mean latency (seconds) |
| --- | --- | --- |
| Compound of the invention (2HCl) | 10 | 185.8 |
| | 30 | 230.0**(1) |

TABLE 1-continued

| Test compound | Dose (mg/kg) | Mean latency (seconds) |
| --- | --- | --- |
| Control group | — | 155.3 |

(1): Significant at $p < 0.01$ (Mann-Whitney U-test) against the control group.

It is evident from Table 1 that the compound of this invention showed a significant anti-carbon dioxide induced amnesia activity.

TEST EXAMPLE 2

Anti-hypoxic activity (1) Brain protection against complete ischemia by decapitation:

Testing method

Male mice of the ddY strain (body weight 20-25 g, 5 per group) were orally given the compound of the invention (dihydrochloride) dissolved in 1% gum arabic solution. One hour later, the mice were decapitated, and the time elapsed until a gasping-like mouth opening movement appearing after decapitation ceased (gasping persistent time) was measured, and compared with that obtained with the control group (the group to which 1% gum arabic solution was administered.

Test results

The results are shown in Table 2.

TABLE 2

| Test compound | Dose (mg/kg) | Mean gasping persistent time (%) (1) |
| --- | --- | --- |
| Compound of the invention (2HCl) | 10 | 107 ± 6 |
| | 30 | 139 ± 6** (2) |
| | 100 | 187 ± 8** |

(1): The value obtained when the value of the control group is taken as 100% is expressed by mean ± standard error.
(2): Significant at $p < 0.01$ (Student t-test) against the control group It is clearly seen from Table 2 that the compound of this invention showed a significant activity of prolonging the gasping persistent time.

(2) Brain protection against normobaric hydpoxia

Testing method

Male mice of the ddY strain (body weight 20-25g, 5 per group) were orally administered with the compound of the invention (dihydrochloride) dissolved in a 1% gum arabic solution. One hour after the adminstration, the mouse was put in a transparent plastic container (capacity 27 liters) through which 100% nitrogen was passed at a rate of 80 liters/min. The time elasped until the animal died (the survival time) was measured, and compared with that obtained with the control group (the group to which 1% gum arabic solution was administered).

Test results

The results are shown in Table 3.

TABLE 3

| Test compound | Dose (mg/kg) | Survival time (%) |
| --- | --- | --- |
| Compound of the invention | 10 | 122 ± 5 [(1)**(2)] |

TABLE 3-continued

| Test compound | Dose (mg/kg) | Survival time (%) |
|---|---|---|
| (2HCl) | 30 | 151 ± 7** |

(1): The value obtained when the value of the control group is taken as 100% is expressed by mean ± standard error.
(2): Significant at p < 0.01 (Student t-test) against the control group.

It is clear from Table 3 that the compound of this invention showed a significant activity of prolonging the survival time.

TEST EXAMPLE 3

Lipid peroxide formation inhibiting activity (antioxidant activity):

Testing method

The effect of the test compound on the formation of lipid peroxide by autoxidation was determined by the amount of malondialdehyde (MDA) formed.

Rats were decapitated, and the cerebrum was taken out and homogenized with 4 ml, per gram of the cerebrum, of 50 mM phosphate saline-buffer (pH 7.4) and centrifuged (2800 rpm, 10 minutes). The supernatant was taken into a 10 ml test tube to obtain a brain homogenate. It was frozen at −70° C. and stored.

The brain homogenate was defrozen, and immediately then, diluted to 10-fold with the aforesaid phosphate saline-buffer. A 2 ml portion of the dilution was taken into a 10 ml test tube cooled with ice, and used to measure its antioxidant activity. Twenty microliters of an aqueous solution of the compound of this invention (dihydrochloride) was added. The amount of MDA immediately after the addition was measured as shown below ($MDA_{0\ time}$). The mixture was incubated at 37° C. for 30 minutes. The reaction was stopped by adding 400 microliters of 35% perchloric acid solution. After cooling with ice, the cooled mixture was centrifuged (2800 rpm, 10 minutes). To 1 ml of the supernatant, 0.5 ml of 0.5 % thiobarbituric acid solution dissolved in 50% acetic acid solution was added, and the mixture was heated at 100° C. for 15 minutes. After cooling with ice, the absorbance of the solution at 532 nm was measured, and the amount of MDA formed was determined ($MDA_{test}$).

As a control, the amount of MDA ($MDA_{cont}$) was determined as above.

The antioxidant activity of the compound of the invention was expressed in terms of percent inhibition of autoxidation on the brain homogenate. The calculation was based on the following equation.

$$\text{Antioxidant activity (\%)} = \left(1 - \frac{MDA_{test} - MDA_{0\ time}}{MDA_{cont} - MDA_{0\ time}}\right) \times 100$$

Test results

The test results are shown in Table 4.

TABLE 4

| Test compound | Antioxidant activity (n = 4) | | 50% inhibition concentration (IC$_{50}$) |
|---|---|---|---|
| | (μM) | Mean ± standard error (%) | (μM) |
| Compound of the invention (2HCl) | 10 | 6.4 ± 7.7 | 52 |
| | 30 | 27.1 ± 6.8 | |
| | 100 | 77.9 ± 3.1 | |
| | 300 | 93.4 ± 2.2 | |

The amount of MDA formed in the control group was 234.5±21.0 n mol/g-wet tissue (n=4).

It is clear from Table 4 that the compound of this invention showed the activity of inhibiting formation of lipid peroxide (antoxidant activity).

TEST EXAMPLE 4

Anti-scopolamine-induced amnesia activity:

Testing method

Male mice of the ddY strain (body weight 20–25g, 20 per group) were used, and the activity of the test compound on deficit of memory induced by scopolamine hydrobromide (a muscarinic acetylcholine receptor antagonist) was examined using one-trial passive avoidance response as an index.

Using the same experimental device as in Test Example 1, the same acquisition trial and retrieval trial as in Test Example 1 were carried out (one-trial passive avoidance response.)

Scopolamine hydrobromide (1 mg/kg) was intraperitoneally (i.p.) administered to the animals 20 minutes before the acquisition trial. The compound of the invention (dihydrochloride) was dissolved in 1 % gum arabic solution, and intraperitoneally adminstered immediately after the acquisition trial, and orally (p.o.) administered 60 minutes before the acquisition trial.

A 1% solution of gum arabic was administered to the control group.

Test results

The results are shown in Table 5.

TABLE 5

| Test compound | Dose (mg/kg) (1) | Administration route | Mean latency (seconds) |
|---|---|---|---|
| Compound of the invention (2HCl) | 3 | i.p. | 190.4**(2) |
| | 10 | i.p. | 185.1** |
| | 30 | i.p. | 208.7** |
| Control group | — | i.p. | 92.0 |
| Compound of the invention (2HCl) | 10 | p.o. | 59.8 |
| | 30 | p.o. | 144.6** |
| Control group | — | p.o. | 63.1 |

(1): Concentration calculated as the free base.
(2): Significant at p>0.01 (Mann-Whitney U-test) as against the control group.

It is clear from Table 5 that the compound of this invention showed a significant anti-scopolamine-induced amnesia activity.

TEST EXAMPLE 5

Acute toxicity:

Testing method

Male ddY mice (body weight 20–26 g, 5 per group) were allowed to fast overnight. The compound of this invention (dihydrochloride) dissolved in distilled water was orally (p.o.) administered. From the number of dead animals counted one week later, the $LD_{50}$ (p.o.) was calculated by the Weil method.

Then, the compound of this invention (dihydrochloride) was dissolved in saline and intraperitoneally (i.p.) administered to the mice, and the $LD_{50}$ value (i.p.) was measured similarly.

Test results

The results are shown in Table 6.

TABLE 6

| Test compound | Administration route | $LD_{50}$ (mg/kg) |
|---|---|---|
| Compound of the invention (2HCl) | p.o. | 1,267 |
|  | i.p. | 220 |

The following Examples illustrate the present invention more specifically.

EXAMPLE 1

2-(4-Allyl-1-piperazinyl)-4(3)-quinazolinone (compound of formula I):

N-allylpiperazine (37 g) was added to 30 g of 2-ethylthio-4(3H)-quinazolinone [J. Med. Chem., 11, 392 (1968)], and the mixture was stirred at 140° to 160° C. for 5 hours in a stream of nitrogen. After cooling, the reaction mixture was suspended in ethyl acetate and filtered. The resulting crude crystals were recrystallized from ethanol/ethyl acetate to give 35 g of 2-(4-allyl-1-piperazinyl)-4(3H)-quinazolinone.

Melting point: 195.0°–197.5° C.
NMR (CDCl$_3$, δ ppm): 2.57–2.64 (4H), 3.08 (2H, d), 3.80–386 (4H), 5.19–5.29 (2H, m), 5.83–5.99 (1H, m), 7.13–8.06 (4H).
Elemental analysis (for $C_{15}H_{18}N_4O$):
Calculated (%): C, 66,65; H, 6.71; N, 20.73.
Found (%): C, 66.75; H, 6.73; N, 20.51.

EXAMPLE 2

2-(4-Allyl-1-piperazinyl)-4-chloroquinazoline (compound of formula VI):

Phosphorus oxychloride (10 ml) was added to 10g of 2-(4-allyl-1-piperazinyl)-4(3H)-quinazolinone, and the mixture was heated under reflux for 3 hours. The reaction mixture was poured into ice water, and an aqueous solution of sodium hydroxide was added to neutralize it. The precipitated crystals were collected by filtration. The crystals were dissolved in ethyl acetate and washed with water. The ethyl acetate layer was dried over anhydrous magnesium solufate, and the solvent was evaporated under reduced pressure. The residue was recrystallized from hexane to give 10 g of 20-(4-allyl-1-piperazinyl)-4-chloroquinazoline.

Melting point: 65.0°–68.0° C.
NMR (CDCl$_3$, δ ppm): 2.51–2.57 (4H), 3.05 (2H, d), 3.93–3.99 (4H), 5.16–5.27 (2H, m), 5.83–5.99 (1H, m), 7.19–7.99 (4H).
Elemental analysis (for $C_{15}H_{17}ClN_4$):
Calculated (%): C, 62.39; H, 5.93; N, 19.40.
Found (%): C, 62.50; H, 5.96; N, 19.49.

EXAMPLE 3

2-Chloro-4-pentyloxyquinazoline (compound of formula VIII):

7.3 g of 2,4-dichloroquinazoline (J. Chem. Soc., 1947, 775) was suspended in 40 ml of N,N-dimethylformamide, and with ice cooling, 1.9 g of sodium hydride (oily, 60 %) was added. A solution of 3.7 g of l-pentanol in 5 ml of N,N-dimethylformamide was added dropwise over 5 minutes, and then further stirred at 50° C. for 1 hour. After cooling, the reaction mixture was poured into ice water, and extracted with ethyl acetate. The ethyl acetate layer was washed with water, and dried over anhydrous magnesium sulfate, and the solvent was evaporated under reduced pressure. The resulting residue was subjected to silica gel column chromatography [eluted with hexane/ethyl acetate (8:1, v/v)] to give 8 g of 2-chloro-4-pentyloxyquinazoline. A portion of this produce was recrystallized from hexane to give a product having the following physical property values.

Melting point: 32.0°–34.0 ° C.
NMR (CDCl$_3$, δ ppm): 0.94 (3H, t), 1.33–1.56 (4H, m), 1.89–2.00 (2H, m), 4.61 (2H, t), 7.53–8.18 (4H).
Elemental analysis (for $C_{13}H_{15}ClN_2O$):
Calculated (%): C, 62.28; H, 6.03; N, 11.17.
Found (%): C, 62.30; H, 6.07; N, 11.15.

EXAMPLE 4

2-(4-Allyl-1-piperazinyl)-4-pentyloxyquinazoline (production by process A):

In 30 ml of N,N-dimethylformamide was suspended 3.6 g of 2-(4-allyl-1-piperazinyl)-4(3H)-quinazolinone obtained in Example 1. With stirring under ice cooling, 3.6 g of pentyl iodide and 0.95 g of sodium hydride (oily, 60 %) were added to the suspension. The mixture was then stirred at 60° C. for 2.5 hours. Ice water (100 ml) was added to the reaction mixture, and the mixture was extracted with ethyl acetate. The ethyl acetate layer was washed with water, dried over anhydrous magnesium sulfate, and concentrated under reduced pressure. The residue was subjected to silica gel column chromatography [eluted with chloroform/methanol (30:1, v/v)] to give 4.0 g of 2-(4-allyl-1-piperazinyl)-4-pentyloxyquinazoline as a pale yellow oil.

Boiling point: 164°–167° C. (0.2 mmHg)
NMR (CDCl$_3$, δ ppm): 0.95 (3H, t), 1.35–1.55 (4H, m), 1.82–1.92 (2H, m) 2.51–2.57 (4H), 3.06 (2H, d), 3.92–3.97 (4H), 4.47 (2H, t), 5.16–5.27 (2H, m), 5.84–6.00 (1H, m), 7.08–7.94 (4H).
Elemental analysis (for $C_{20}H_{28}N_4O$):
Calculated (%): C, 70.55; H, 8.29; N, 16.46.
Found (%): C, 70.56; H, 8.11; N, 16.32.
Dihydrochloride Ten milliliters of 10% (w/w) hydrochloric acid-ethanol was added to 3.4 g of 2-(4-allyl-1-piperazinyl)-4-pentyloxyqinazoline, and 30 ml of ethyl acetate was added to this solution. The precipitated crystals were dissolved by heating. After cooling, the precipitated crystals were collected by filtration to give 2.7 g of 2-(4-allyl-1-piperazinyl)-4-pentyloxyquinazoline dihydrochloride as colorless needles.

Melting point: 260° C. (dec.)
NMR (DMSO-d$_6$/D$_2$O, δ ppm): 0.92 (3H, t), 1.31–1.51 (4H, m), 1.80–1.91 (2H, m), 3.15–5.20 (12H), 5.57–5.63 (2H, m), 5.94–6.08 (1H, m), 7.50–8.08 (4H).
Elemental analysis (for $C_{20}H_{28}N_4O$ 2HCl):
Calculated (%): C, 58.11; H, 7.31; N, 13.55.
Found (%): C, 58.07; H, 7.30; N, 13.54.

Sesquifumarate

Ethanol (33 ml) was added to 2.7 g of fumaric acid, and the mixture was heated to form a solution. A solution of 4.0 g of 2-(4-allyl-l-piperazinyl)-4-pentyloxyqyinazoline in 5 ml of ethanol was added to the resulting solution. The mixture was cooled, and the precipitated crystals were collected by filtration and recrystallized from ethanol to give 1.7 g of 2-(4-allyl-l-piperazinyl)-4-pentyloxyquinazoline sesquifumarate as colorless needles.

Melting point: 141.5°–144.5° C.

NMR (DMSO-$d_6$, $\delta$ ppm): 0.90 (3H, t), 1.30–1.49 (4H, m), 1.76–1.90 (2H, m), 2.53–2.57 (4H), 3.09 (2H, d), 3.82–3.88 (4H), 4.48 (2H, t), 5.18–5.29 (2H, m), 5.80–5.95 (1H, m), 6.62 (3H, s), 7.15–7.89 (4H).

Elemental analysis (for $C_{20}H_{28}N_4O \cdot 3/2 C_4H_4O_4$):
Calculated (%): C, 60.69; H, 6.66; N, 10.89.

Dimaleate

Ethanol (25 ml) was added to 2.3 g of maleic acid, and the mixture was heated to form a solution. A solution of 3.4 g of 2-(4-allyl-l-piperazinyl)-4-pentyloxyquinazoline in 5 ml of ethanol was added to the solution. The mixture was cooled, and the precipitated crystals were collected by filtration and recrystallized from 90 % ethanol to give 3.3 g of 2-(4-allyl-l-piperazinyl)-4-pentyloxyquinazoline dimaleate as colorless needles.

Melting point: 174.0°–177.0° C.

NMR (DMSO-$d_6$, $\delta$ ppm): 0.92 (3H, t), 1.31–1.51 (4H, m), 1.78–1.89 (2H, m), 3.14–4.54 (12H), 5.50–5.57 (2H, m), 5.87–6.03 (1H, m), 6.16 (4H, s), 7.24–7.95 (4H).

Elemental analysis (for $C_{20}H_{28}N_4O \cdot 2 C_4H_4O_4$):
Calculated (%): C, 58.73; H, 6.34; N, 9.78.
Found (%): C, 58.73; H, 6.35; N, 9.80.

EXAMPLE 5

2-(4-Allyl-l-piperazinyl)-4-pentyloxyqyionazoline (production by process B):

The 2-(4-allyl-l-piperazinyl)-4-chloroquinazoline (3.0 g) obtained in Example 2 was suspended in 20 ml of N,N-dimethylformamide, and under ice cooling, 1 g of 1-pentanol and 0.5 g of sodium hydride (oily, 60 %) were added. The mixture was then stirred at room temperature for 4 hours. The reaction mixture was poured into ice water, and extracted with ethyl acetate. The ethyl acetate layer was washed with water, and dried over anhydrous magnesium sulfate. The solvent was concentrated under reduced pressure, and the residue was subjected to silica gel column chromatography [eluted with chloroform/methanol (30:1, v/v)] to give 2-(4-allyl-l-piperazinyl)-4-pentyloxyquinazoline as a pale yellow oil.

The physical property values of this product agreed with those of the 2-(4-allyl-l-piperazinyl)-4-pentyloxyqyinazoline produced in Example 4.

EXAMPLE 6

2-(4-allyl-l-piperazinyl)-4-pentyloxyqyinazoline (production by process C):

The 2-chloro-4-pentyloxyqyinazoline (7.5 g) obtained in Example 3 was dissolved in 30 ml of ethanol, and 8 g of N-allypiperazine was added. The mixture was heated under reflux for 2 hours. After cooling, the reaction mixture was poured into ice water and extracted with ethyl acetate. The ethyl acetate layer was washed with water, and dried over anhydrous magnesium sulfate. The solvent was concentrated under reduced pressure. The residue was subjected to silica gel column chromatography [eluted with chloroform/methanol (30:1, v/v)] to give 8.6 g of 2-(4-allyl-l-piperazinyl)-4-pentyloxyquinazoline as a pale yellow oil.

The physical property values of this produce agreed with those of the 2-(4-allyl-l-piperazinyl)-4-pentyloxyqyinazoline produced in example 4.

EXAMPLE 7

[Formulation of tablets]

| Component | Amount (g) |
| --- | --- |
| 2-(4-Allyl-l-piperazinyl)-4-pentyloxyquinazoline dihydrochloride | 100 |
| Lactose | 890 |
| Crystalline cellulose | 900 |
| Carboxymethyl cellulose calcium | 70 |
| Talc | 25 |
| Magnesium stearate | 15 |
| Total | 2000 |

[Procedure]

The above ingredients were uniformly mxied, and tabletted to form tablets each weighing 200 mg.

EXAMPLE 8

[Formulation of a powder]

| Component | Amount (g) |
| --- | --- |
| 2-(4-Allyl-l-piperazinyl)-4-pentyloxyquinazoline dihydrochloride | 20 |
| Lactose | 580 |
| Starch | 400 |
| Total | 1000 |

[Procedure]

The above ingredients were fully mixed to form a uniform mixed powder containing 20 mg of the active ingredient per gram.

EXAMPLE 9

[Formulation of an injectable preparation]

Five grams of 2-(4-allyl-l-piperazinyl)-4-pentyloxyquinazoline dihydrochloride was dissolved in injectable distilled water to form 1000 ml of a solution. The solution was sterilized and filtered and put in an amount of 1 ml into each ampoules, and the ampoules were sealed up.

What is claimed is:

1. A quinazoline compound of the formula

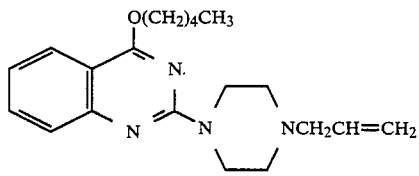

or a pharmacologically acceptable acid addition salt thereof.

2. A composition for remedying cerebral dysfunction comprising a pharmaceutically effective amount of a quinazoline compound of the formula

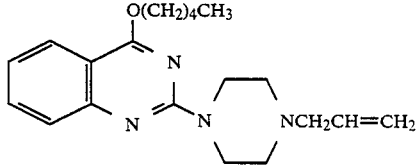

or a pharmacologically acceptable acid addition salt thereof and a pharmaceutically acceptable carrier or diluent therefor.

* * * * *